US006444198B1

(12) United States Patent
Daggy et al.

(10) Patent No.: US 6,444,198 B1
(45) Date of Patent: Sep. 3, 2002

(54) EFFERVESCENT LAXATIVES

(75) Inventors: Bruce P. Daggy, Slough (GB); Kenneth G. Mandel, Parsippany, NJ (US)

(73) Assignee: SmithKline Beecham Corporation, Philadelphia, PA (US)

( * ) Notice: Subject to any disclaimer, the term of this patent is extended or adjusted under 35 U.S.C. 154(b) by 0 days.

(21) Appl. No.: 10/071,638

(22) Filed: Feb. 7, 2002

Related U.S. Application Data

(63) Continuation of application No. 09/913,685, filed as application No. PCT/US00/04701 on Feb. 22, 2000.
(60) Provisional application No. 60/121,089, filed on Feb. 22, 1999.

(51) Int. Cl.[7] ............................................. A61K 31/74
(52) U.S. Cl. .................................................... 424/78.01
(58) Field of Search ....................................... 424/78.01

(56) References Cited

U.S. PATENT DOCUMENTS

| | | |
|---|---|---|
| 4,946,939 A | 8/1990 | Murphy et al. |
| 4,948,591 A | 8/1990 | Yamada |
| 5,077,048 A | 12/1991 | Kimura et al. |
| 5,124,144 A | 6/1992 | Giorgetti et al. |
| 5,710,183 A | 1/1998 | Halow |
| 6,048,901 A | 4/2000 | Cleveland et al. |
| 6,132,767 A | * 10/2000 | Borody et al. ............... 424/456 |

FOREIGN PATENT DOCUMENTS

| | | |
|---|---|---|
| BE | 671274 | 2/1966 |
| CH | DE 3807712 A1 | 7/1987 |
| GB | 1120904 | 10/1965 |
| JP | 4-198126 | 7/1995 |
| RU | 2111741 C1 | 10/1994 |
| WO | WO 87/00754 | 2/1987 |

OTHER PUBLICATIONS

Hammer et al., "Studies of Osmotic Diarrhea Induced in Normal Subjects by Ingestion of Polyethylene Glycol and Lactulose", J. Clin. Invest, Oct. 1989, vol. 84, pp. 1056–1062.
Davis et al., "Development of a Lavage Solution Associated with Minimal Water and Electrolyte Absorption or Secretion", Gastroenterology, 1980, vol. 78, pp. 991–995.
Hudziak, et al., "Le polyethylene glycol 4000 a faible dose: effets digestifs", Gastroenterol Clin. Biol., 1996, vol. 20, pp 418–423 (article & translation).
Bernier et al., "Effet du polyethylene glycol 4000 a petities doses sur la consistance et l'eau de dilution des selles chez le sujet sain", Gastroenterol Clin. Biol., 1997, vol. 21 (article & translatin).
Baldonedo, et al., "Evaluacion Y Uso Del Polietilen Glicol En Pacientes Constipados", Gen, Revista de la Sociedad Venezolana de Gastroenterologia, 1991, vol. 45(4), pp. 294–297 (aricle & translation).

* cited by examiner

Primary Examiner—James H Reamer
(74) Attorney, Agent, or Firm—Dara L. Dinner; Stephen Venetianer; Charles M. Kinzig

(57) ABSTRACT

The present invention is directed to a novel osmotic/effervescent system for the treatment of constipation and fecal impaction in a human or mammal in need thereof.

14 Claims, No Drawings

EFFERVESCENT LAXATIVES

The accompanying application is a Continuation of prior application ser. No. 09/913,685 filed Aug. 16, 2001 which is a §317 national stage filing of PCT/US00/04701 filed Feb. 22, 2000 which claims benefit from provisional application No. 60/121,089 filed Feb. 22, 1999.

FIELD OF THE INVENTION

The present invention is directed to a novel over-the-counter (OTC) laxative as an improved, replacement therapy to current stimulant laxatives.

BACKGROUND OF THE INVENTION

Within the next 2 to 3 years, the Food and Drug Administration (FDA) appears likely to discontinue OTC approval of several current stimulant laxatives. Over the last decade, positive carcinogenicity and/or genotoxicity results have resulted in FDA banning danthron (mid-1980's) and in 1997, the FDA delisted phenolphthalein as an OTC laxative due to safety issues.

Specifically, in June 1998, the FDA has continued to pressure the OTC stimulant laxative category, reclassifying remaining approved stimulants: senna, cascara, aloe, bisacodyl, from Category I (safe and effective) to Category III (more data needed), and requiring manufacturers to provide updated carcinogenicity and genotoxicity evaluations for these laxative actives. Failure to meet this mandate, and/or prove safety will result in further delisting of laxative actives from the tentative final monographs (TFM), (Fed. Reg. 63: 33592–33595, Jun. 19, 1998). Indeed, in a recent review of scientific literature, van Gorkom et al., concluded that anthranoid laxatives, which include the active moieties in senna extracts, and the chemical laxatives phenolphthalein bisacodyl, can have a potential role in both promotion and initiation of tumorgenesis, and may be associated with increased risk for colorectal cancer (van Gorkom, B. A. P.; de Vries, E. G. E.; Karrenbeld, A.; Kleibeuker, J. H. Anthranoid laxatives and their potential carcinogenic effects. Alimentary Pharmacology & Therapeutics, Vol. 13: pp. 443–452, 1999. Hence the potential for further delistings are strong.

Hence, there is a strong potential for dramatic change to this segment of the OTC laxative market over the next several years. If the events which followed the FDA action to ban phenolphthalein recur, any FDA action will be followed by similar delisting in other countries.

While bulk fiber products, such as Metamucil® and Citrucel®, are presently available, a large number of individuals have found that these products have unacceptable product aesthetics (e.g., taste, viscosity, volume etc). Therefore new alternative therapies to these bulk fiber laxatives based on ease of use and aesthetic properties are desired.

One group of the newer alternative therapies for bowel cleansing prior to colonoscopic exam or GI surgery are the prescription isosmotic bowel evacuant solutions, such as Golytely® and Nulytely® (Braintree Labs, Braintree, Mass., USA). Similar prescription products are marketed in the US by Colyte® by Schwarz Pharma, and in Europe an osmotic laxative by Movicol® (Norgine, Lmtd., Middlesex, UK). Recently, a new laxative containing only polyethylene glycol 3350 NF, has also been introduced in the US (Miralax®, Braintree Labs, Braintree, Mass., USA), where it is available only by prescription.

All of these products contain polyethylene glycol (PEG) as the active ingredient. In most products, the PEG is mixed with various salts to provide a laxative action with osmotic balance. This is required when the products are used in the high volumes (2–4 L) required for colonic purgation and cleansing. In high volume these PEG-containing agents provide excellent colonic cleansing prior to GI surgical or colonoscopic procedures. They neither stimulate water and electrolyte secretion into the GI tract, nor do the products result in significant water and electrolyte absorption; essentially, the volume of ingested liquid simply passes through the GI tract. For this indicated usage as a bowel evacuant, patients are instructed to drink 2 to 4 liters over several hours.

U.S. Pat. No. 5,710,183, Halow, G., discloses a PEG composition with a fiber bulking agent for clinical treatment of constipation and/or diarrhea.

U.S. Pat. No. 5,124,144, Castagnola et al., discloses what is a PEG/electrolyte product for use as a cathartic laxative.

WO 87/00754, Fordtran, J., discloses a low-sodium laxative and lavage solution containing PEG with various electrolytes added such as sodium, potassium, chloride and bicarbonate.

DE 3807712, Deyhle et al., discloses a laxative formulation also containing electrolytes, PEG, alkali hydrogen carbonate and citric acid.

RU 2111741, Chumak et al. discloses use of a reduced lavage volume, 2 liters, of PEG with an electrolyte solution. The electrolyte mixture contains sodium bicarbonate and citric acid which may be in an amount sufficient to provide effervescence.

WO 98/43654, Jacob et al., is directed towards a non-aqueous colonic purgative containing magnesium salts and potentially polyethylene glycol.

JP 4198126 OTSUKA PHARM CO LTD discloses a liquid preparation of PEG and electrolytes along with α-aminoacid, for colon irrigation. The α-amino acids are used as antioxidants to stabilize PEG and prevent formation of formaldehyde. This was an attributed problem of PEG-based laxatives early in their product life. Use of the highly purified PEG's today overcome these issues. The levels of product 0.01% range (0.1 g/L) are also too low to provide any appreciable effervescence.

SUMMARY OF THE INVENTION

The present invention is directed to a pharmaceutical formulation comprising polyethylene glycol (PEG) 3350, and a pharmaceutically acceptable effervescent coupling system.

Another aspect of the present invention is a method of administering to a mammal, an effective amount of the above noted pharmaceutical formulation for the treatment of constipation, or for the treatment of fecal impaction, in a mammal in need thereof.

DETAILED DESCRIPTION OF THE INVENTION

The present invention is directed towards an effervescent formulation of an osmotic bowel evacuant solution, such as a polyethylene glycol based product. These formulations provide for an acceptable level of laxative efficacy, with superior safety advantages over current stimulants, which are under FDA review for safety concerns. Further, these formulations should be safe and appropriate for use in pediatric constipation.

The effervescent/PEG osmotic formulation offers an alternative that provides for a new, and safe, product as a replacement to the current technologies. The PEG based osmotic formulations have proven to be both safe and highly physician recommended.

However, an effervescent/PEG based formulation, for use as an OTC laxative would require consumption of a much smaller volume, such as one or two 4–8 oz doses over a 24 hour period. Several published studies have shown utility of the PEG-based technology for use as a laxative with low-volume dosage. E. Corazziari, D. Badiali, F. L. Habib, G. Reboa, G. Pitto, G. Mazzacca, F. Sabbatini, R. Galeazzi, Te, Cilluffo, I. Vantini, E. Bardelli, F. Baldi. Small volume isosmotic polyethylene glycol electrolyte balanced solution (PMF-100) in treatment of chronic nonorganic constipation. Digestive Diseases & Sciences, Vol. 41: 1636–1642, 1996.

J. A. DiPalma, P. H. deRidder, R. C. Orlando, B. E. Kolts, M. v. B. Cleveland. A randomized placebo-controlled, multicenter study of the safety and efficacy of Braintree 851 laxative. Gastroenterology, Vol. 112: A722, 1997.

P. Culbert, H. Gillett, A. Ferguson. Highly effective oral therapy (polyethylene glycol/electrolyte solution) for faecal impaction and severe constipation. Clinical Drug Investigation, Vol. 16: 355–360, 1998.

A. Attar, M. Lemann, A. Ferguson, M. Halphen, M.-C. Boutron, B. Flourie, E. Alix, M. Salmeron, F. Guillemot, S. Chaussade, A.-M. Menard, J. Moreau, G. Naudin, M. Barthet. Comparison of a low dose polyethylene glycol electrolyte solution with lactulose for treatment of chronic constipation. Gut, Vol. 44: 226–230, 1999.

Therefore, one aspect of the present invention is the use of an osmotic acting composition containing polyethyleneglycol based systems, (preferably, PEG 3350 NF, or PEG 4000 NF, in combination with an effervescent coupling system, which is diluted with a suitable volume of a liquid, such as water, or juice.

The effervescent couple comprises a basic ingredient and an acidic ingredient, the basic ingredient liberating carbon dioxide when it and the acidic ingredient are contacted with added water.

The amount of the effervescent couple is selected at a level sufficient to cause a "fizzy reaction" without itself causing discomfort in the patients mouth.

The effervescent couple typically comprises citric acid or sodium hydrogen citrate and sodium bicarbonate, but other physiologically acceptable acid/alkaline or alkaline earth metal carbonate mixtures may be used, for example tartaric, adipic, fumaric or malic acids, and sodium, potassium or calcium (bi)carbonates or sodium glycine carbonate.

In general it has been found that preferred taste characteristics are exhibited when the relative proportions of the components of the effervescent couple on a chemical molecular equivalent basis are in the range of 3:1 to 3:4, more preferably about 1.4 to 1.9:1, expressed as the ratio of molecular equivalents of the basic component to the acidic component, where the basic and acid components are sodium bicarbonate ($NaHCO_3$) and citric acid, respectively. However, it is possible to utilize much less bicarbonate and acid than a number of well known effervescent systems. The examples herein will demonstrate usefulness of high and low levels of effervescent coupling reagents. In terms of a preferred combination of sodium bicarbonate and citric acid, these values represent on a weight basis, a range from 3:1 to 0.6–0.8:1, preferably approximately 1:1 expressed as the ratio of basic to acidic component.

However, in some formulations, the choice of flavouring agents may result in optimization of taste characteristics when there is an excess of acidic component, for example, on a chemical molecular equivalent basis of from about 11:3 to 4:3 expressed as the ratio of acidic to basic component. For the combination of citric acid and sodium bicarbonate this may represent 5:1 to 1:1 on a weight basis.

The weight of the acidic component in the formulation may be in the range 7% to 31%, preferably 9% to 18%, by weight.

The weight of the basic component in the formulation may be in the range 7% to 32%, preferably 9% to 18%, by weight.

Preferred combinations comprise sodium bicarbonate with citric acid (or sodium hydrogen citrate) or malic acid in a weight ratio of 2:1 to 1:1.

Other preferred combinations may substitute potassium bicarbonate for part or all of the sodium bicarbonate as the basic component of the effervescent couple. To maintain molecular equivalence, substitution of potassium bicarbonate for sodium bicarbonate is at a ratio of approximately 1.2:1. Potassium bicarbonate can be used with any of the above acid components.

The preferred level of the coupling agents, preferably bicarbonate and citrate for an effervescence mixture, is about 2.3 gram $NaHCO_3$ (sodium bicarbonate) and 2.2 gram citric acid. This dose provides very significant ANC (acid neutralizing capacity) approximately 20 mEq. However, the levels can be reduced by a factor of 4–5 and still provide some degree of effervescence (e.g., 0.5 g $NaHCO_3$ and 0.4 g citric acid).

It is recognized that additional excipients may be added to the formulation, such as flavouring agents, colouring agents, sweetning agents, antioxidants, and other well known agents for stability and packaging considerations.

A preferred PEG for use herein is PEG 3350, a nonabsorbable and inert polymer of about 3,000 molecular weight. Generally, the range of PEG 3350 for a 125 to 240 ml reconstitution in liquid will be from a about 5 grams to about 30 gms, preferably from about 10 to about 20 gms, more preferably 13 to 17 grams. Treatment may be once or more daily, up to 4 times daily, but preferably once daily.

In contrast to bulk-fibers, the resulting effervescent/PEG-based formulations when made into a liquid dosage, are non-viscous and are optimally be provided to consumers as either bulk powder, or preferably as single dose powder sachets, for dissolution in a suitable liquid, such as water or juice. The product would dissolve rapidly (within seconds) and completely, and does not thicken on standing.

Based on volume consumed (e.g., one or two 4–8 oz doses), performance attributes would be consistent with those presently desired by stimulant laxative users (rapid action, clean-out), but without the negative side-effects of cramping and gas, and without systemic exposure potentially harmful agents.

The required dosage for use as a laxative may be one which is equivalent to the "minimally effective dose", i.e., one that requires 2 to 3 days treatment before significant effect, having a similar onset and action to the bulk fiber based laxatives. Or the dosage could be increased to be equivalent in action to the current stimulant based products, having an earlier onset of action (a few hours to overnight).

The present invention is useful as primary treatment for both occasional and chronic constipation, and for the treatment of fecal impaction (at a higher dose). Another aspect of the present invention is the treatment of upper GI symptoms associated with such constipation, such as heartburn or bloating. Suitably, the composition herein may also be used for other constipation related disorders, such as irritable bowel syndrome, diverticular disease, and hemorrhoids.

METHODS OF PREPARATION

The following examples illustrates the invention but is not intended to limit the scope thereof. All parts and percentages are by weight unless otherwise indicated.

EXAMPLE 1

A preferred example provides as sachet for reconstitution in 240 ml water for use as laxative.
PEG System:
  17.0 g polyethylene glycol (PEG) 3350 NF
Effervescent Coupling Reagents:
  1.50 g NaHCO3
  1.00 g Citric Acid
The PEG solution is combined with effervescent coupling system and packaged as a sachet to be added to a 8 ounce glass of water.

EXAMPLE 2

Another preferred examples provides as sachet for reconstitution in 240 ml water for use as laxative.
PEG System:
  17.0 g polyethylene glycol (PEG) 3350 NF
Effervescent Coupling Reagents:
  2.32 g NaHCO3
  2.18 g Citric Acid
The PEG solution is combined with effervescent coupling system and packaged as a sachet to be added to a 8 ounce glass of water.

EXAMPLE 3

Another preferred examples provides as sachet for reconstitution in 125–180 ml water for use as laxative.
PEG System:
  13.12 g PEG 3350
  0.78 g flavoring ingredients
Effervescent Coupling Reagents:
  2.32 g NaHCO3
  2.18 g Citric Acid
The PEG solution is combined with effervescent coupling system and packaged as a sachet to be added to a 4–6 ounce glass of water.

EXAMPLE 4

Another preferred examples provides as sachet for reconstitution in 125–180 ml water for use as laxative.
PEG System:
  13.12 g PEG 3350
  0.78 g flavoring ingredients
Effervescent Coupling Reagents:
  1.50 g NaHCO3
  1.00 g Citric Acid
The PEG solution is combined with effervescent coupling system and packaged as a sachet to be added to a 4–6 ounce glass of water.

EXAMPLE 5

Provided as sachet for reconstitution in 125–200 ml water for use as laxative.
PEG System:
  8.5 g PEG 3350
  0.06 g flavoring mixture (for flavored product)
Effervescent Coupling Reagents:
  2.32 g NaHCO3
  2.18 g Citric Acid
The PEG solution is combined with effervescent coupling system and packaged as a sachet to be added to a 4–6 ounce glass of water.

EXAMPLE 6

Provided as sachet for reconstitution in 125–200 ml water for use as laxative.
PEG System:
  8.5 g PEG 3350
  0.06 g flavoring mixture (for flavored product)
Effervescent Coupling Reagents:
  1.50 g NaHCO3
  1.00 g Citric Acid
The PEG solution is combined with effervescent coupling system and packaged as a sachet to be added to a 4–6 ounce glass of water.

EXAMPLE 7

Provided as sachet for reconstitution in 125–200 ml water for use as laxative.
PEG System:
  13.125 g PEG 3350
Effervescent Coupling Reagents:
  2.32 g NaHCO3
  2.18 g Citric Acid
The PEG solution is combined with effervescent coupling system and packaged as a sachet to be added to a 4–6 ounce glass of water.

EXAMPLE 8

Provided as sachet for reconstitution in 125–200 ml water for use as laxative.
PEG System:
  13.125 g PEG 3350
Effervescent Coupling Reagents:
  1.50 g NaHCO3
  1.00 g Citric Acid
The PEG solution is combined with effervescent coupling system and packaged as a sachet to be added to a 4–6 ounce glass of water.

EXAMPLE 7

Provided as sachet for reconstitution in 125–200 ml water for use as laxative.
PEG System:
  13.125 g PEG 3350
Effervescent Coupling Reagents:
  2.32 g NaHCO3
  2.18 g Citric Acid
The PEG solution is combined with effervescent coupling system and packaged as a sachet to be added to a 4–6 ounce glass of water.

All publications, including but not limited to patents and patent applications, cited in this specification are herein incorporated by reference as if each individual publication were specifically and individually indicated to be incorporated by reference herein as though fully set forth.

The above description fully discloses the invention including preferred embodiments thereof. Modifications and improvements of the embodiments specifically disclosed herein are within the scope of the following claims. Without further elaboration, it is believed that one skilled in the art can, using the preceding description, utilize the present invention to its fullest extent. Therefore the Examples herein are to be construed as merely illustrative and not a limitation of the scope of the present invention in any way. The embodiments of the invention in which an exclusive property or privilege is claimed are defined as follows.

What is claimed is:

1. A pharmaceutical formulation comprising an osmotic amount of polyethylene glycol (PEG) 3350, or PEG 4000, and a pharmaceutically acceptable effervescent coupling system.

2. The formulation according to claim 1 wherein the effervescent couple comprises about 10 to about 30% of the total weight of the formulation.

3. The formulation according to claim 1 wherein the effervescent couple comprises an acid component selected from citric acid, tartaric acid, adipic acid, fumaric acid, malic acid, or acid salts thereof, or mixtures thereof.

4. The formulation according to claim 1 wherein the effervescent couple comprises an alkaline component selected from sodium, potassium or calcium (bi) carbonates or sodium glycine carbonate.

5. The formulation according to claim 1 which further comprises one or more flavoring, colouring and sweetening agents.

6. The formulation according to claim 1 wherein the PEG is present in an amount of 7.5 to 30 grams per unit dose.

7. The formulation according to claim 1 wherein the PEG is present in an amount of 10 to 20 grams per unit dose.

8. A method of treating constipation in a mammal in need therof, which method comprises administering to said mammal an effective amount of a formulation according to claim 1.

9. A method of treating fecal impaction in a mammal in need thereof, which method comprises administering to said mammal an effective amount of a formulation according to claim 1.

10. The formulation according to claim 1 wherein the formulation is in a unit dose sachet.

11. The formulation according to claim 2 wherein the formulation is in a unit dose sachet.

12. The formulation according to claim 5 wherein the formulation is in a unit dose sachet.

13. The formulation according to claim 6 wherein the formulation is in a unit dose sachet.

14. The formulation according to claim 8 wherein the formulation is in a unit dose sachet.

* * * * *